(12) United States Patent
Boon Von Ochssee

(10) Patent No.: US 12,009,097 B2
(45) Date of Patent: Jun. 11, 2024

(54) WIRELESS COMMUNICATION SYSTEM FOR REMOTE MEDICAL ASSISTANCE

(71) Applicant: Maritime Medical Applications B.V., Rotterdam (NL)

(72) Inventor: Walther Dietmar Boon Von Ochssee, Reno, NV (US)

(73) Assignee: MARITIME MEDICAL APPLICATIONS B.V., Rotterdam (NL)

( * ) Notice: Subject to any disclaimer, the term of this patent is extended or adjusted under 35 U.S.C. 154(b) by 487 days.

(21) Appl. No.: 16/622,617

(22) PCT Filed: Jun. 13, 2018

(86) PCT No.: PCT/NL2018/050386
§ 371 (c)(1),
(2) Date: Dec. 13, 2019

(87) PCT Pub. No.: WO2018/231059
PCT Pub. Date: Dec. 20, 2018

(65) Prior Publication Data
US 2021/0249127 A1    Aug. 12, 2021

(30) Foreign Application Priority Data
Jun. 13, 2017    (NL) .................................... 2019059

(51) Int. Cl.
*G16H 40/63*    (2018.01)
*A61B 5/00*    (2006.01)
(Continued)

(52) U.S. Cl.
CPC .............. *G16H 40/63* (2018.01); *G09B 5/02* (2013.01); *G09B 19/003* (2013.01); *G09G 5/003* (2013.01);
(Continued)

(58) Field of Classification Search
CPC ........ G16H 40/63; G09B 5/02; G09B 19/003; G09G 5/003; G09G 2370/16;
(Continued)

(56) References Cited

U.S. PATENT DOCUMENTS

2012/0200488 A1 *  8/2012  Osterhout ..........  G02B 27/0093
                                                          345/156
2012/0206577 A1 *  8/2012  Guckenberger .....  G09B 19/003
                                                           348/47
(Continued)

FOREIGN PATENT DOCUMENTS

EP              2851830 A1 *  3/2015 ............. G02B 27/00
WO          2017/072616        5/2017
WO     WO-2017072616 A1 *  5/2017 ........... A61B 5/0404

*Primary Examiner* — Thu V Nguyen
*Assistant Examiner* — Angela M Widhalm De Rodriguez
(74) *Attorney, Agent, or Firm* — Peacock Law P.C.; Justin R. Muehlmeyer

(57) ABSTRACT

The present invention relates to a wireless communication system for medical assistance comprising a first mobile device (11) and a second mobile device (12) communicating via a two-directional transmitting system, both mobile devices being configured to display a second optical input (32) from the second mobile device superimposed on a first optical input (31) from the first mobile device; and a use of said wireless system for training and providing medical assistance, wherein assistance is typically provided over a long distance (being remote). The medical assistance is typically provided by well trained professional to laymen that at best have been partly trained.

14 Claims, 3 Drawing Sheets

(51) Int. Cl.
    *A61B 5/021*    (2006.01)
    *A61B 5/145*    (2006.01)
    *G09B 5/02*     (2006.01)
    *G09B 19/00*    (2006.01)
    *G09G 5/00*     (2006.01)
    *H04L 67/131*   (2022.01)

(52) U.S. Cl.
    CPC .......... *H04L 67/131* (2022.05); *A61B 5/0006* (2013.01); *A61B 5/021* (2013.01); *A61B 5/14542* (2013.01); *G09G 2370/16* (2013.01); *G09G 2370/20* (2013.01)

(58) Field of Classification Search
    CPC ... G09G 2370/20; H04L 67/38; A61B 5/0006; A61B 5/021; A61B 5/14542
    See application file for complete search history.

(56) References Cited

U.S. PATENT DOCUMENTS

| | | | |
|---|---|---|---|
| 2014/0204190 A1* | 7/2014 | Rosenblatt, III | G16H 70/20 705/2 |
| 2014/0267662 A1 | 9/2014 | Lampo | |
| 2015/0077502 A1* | 3/2015 | Jordan | G16H 40/67 348/14.03 |
| 2017/0069227 A1* | 3/2017 | Dialameh | G06F 16/955 |
| 2017/0186157 A1* | 6/2017 | Boettger | G06F 3/0304 |

\* cited by examiner

Location 1
Location 2
Device 11 captures Reality 31
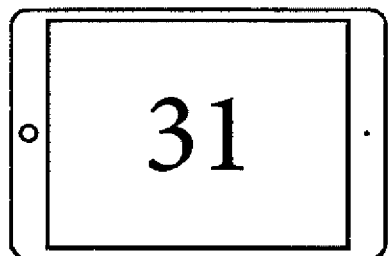
Device 12 captures Reality 32
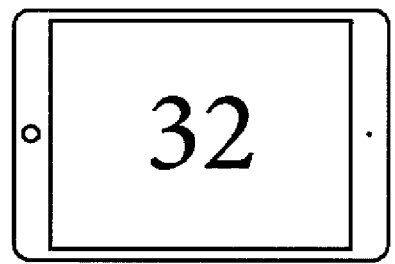
31 + 32
Both realities are augmented and merged
Fig. 2
Augmentation of reality 1 and 2 creates a third reality
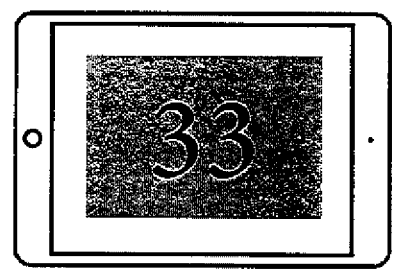
Reality 33 is presented on device 11 using augmented reality
Reality 33 is presented on device 12 using augmented reality

WIRELESS COMMUNICATION SYSTEM FOR REMOTE MEDICAL ASSISTANCE

FIELD OF THE INVENTION

The present invention is in the field of a wireless communication system for medical assistance, and a use of said wireless system for training and providing medical assistance, wherein assistance is typically provided over a long distance. The medical assistance is typically provided by a well trained professional to laymen that at the best have been partly trained.

BACKGROUND OF THE INVENTION

The present invention is in the field of a system for medical assistance wherein assistance is typically provided over a long distance in view of a medical professional not being available on site. For instance on ships and water or airborne vessels no medical trained personnel may be present. Provision of medical care is therefore legally transferred to the captain of the ship and/or a ship's officer. The medical responsible people obtain some basic training, typically delivered on shore. The basic training is found to be insufficient in many cases, partly in view of insufficient experience with many medical cases, sometimes in view of inadequate training for the specific and often complex case, and also in view of lack of familiarity with cases which may result in mental hurdles.

However in many cases the legally responsible people for medical care do have to perform medical actions and carry out medical procedures, sometimes to prevent worse from happening, sometimes to save lives, sometimes to provide accurate care, and so on. In such cases they rely on their basic training and on handbooks or the like. Apart from the fact that training and handbooks are typically outdated at least a few years, they do not provide all the information typically needed to perform the medical actions required; at the best they provide generic information and instructions, which information may be of limited relevance to the case. In addition it is quite often difficult to establish what the medical disorder or disease actually is, especially from handbooks or likewise the internet. Therefore quite often there is a need to consult a medical professional. Apart from the fact that distance, language, time zone, availability, exact knowledge of the professional, etc. are already issues to overcome, the medical professional still has to rely on spoken information from the people in charge of medical care, and vice versa. Especially when time becomes an issue a risk of wrong or inadequate treatment is significant.

Another issue is that the people in charge of medical care, as well as the medical professional, are typically trained in a different location and/or setting. As a consequence a potential risk of inconsistencies is present, which may lead to wrong diagnosis, inadequate treatment, insufficient treatment, neglect of certain aspects of treatment, etc. The "system" of treatment may as a result be considered unreliable and may form a risk for the treatment of the patient, such as in view of claims. Such may especially be the case for ships and vessels out at sea.

In addition communication over these long distance may be hampered by stability or insufficient capabilities of a communication system used, such as bandwidth, noise, disturbances, etc.

In principle complex and costly systems might be used to overcome some of the problems mentioned, but these are not used in practice, not even on very large ships.

Some prior art not particularly relevant to the present invention is US2017/069227 A1, WO 2017/072616 A1 and US2015/0077502 A2. US2017/069227 A1 recites a system and method for providing real-time object recognition. Such is not a goal of the present invention; further recognized objects are not physical reality, but a representation thereof. The recognized objects are provided as tactile or audio feedback to a typically optically disabled user. Only one end-user is involved. WO 2017/072616 A1 recites a remote assistance workstation for remote assistance using AR glasses, which may be regarded as a classical one-way system. The goal is to assist people when using AED's, electrodes or metronome in case of acute medical situations. However the system is not symmetrical and there is no two-way augmentation on both ends of the system. The users are not visible to each other. US2015/0077502 A2 recites a GUI which is in any case background art to the present invention.

The present invention relates to a wireless communication system for medical assistance, and a use of said wireless system for training and providing medical assistance, wherein assistance is typically provided over a long distance, which overcome one or more of the above disadvantages, without jeopardizing functionality and advantages.

SUMMARY OF THE INVENTION

The present invention relates in a first aspect to a wireless communication system according to claim 1. The present system is wireless in view of too large distances typically being present between the person in charge of providing medical care and a medical professional, or in view of physical inability for a professional to be present. The system is intended for providing medical assistance typically to the person in charge thereof. It is specifically noted for some jurisdictions that said assistance does not relate to non-statutory subject-matter, such as methods of treatment, surgery, therapy, or diagnosis, but at the most to providing information and instructions to that extend. As mentioned above said person may be regarded to be largely a layman, despite of some training. In order to provide proper instructions it has been found essential that the layman can make use of a simple device, such as a mobile phone, a tablet, a smart phone, or even a (small) computer, which device is typically available. The device should have a display in order to present optical (visual) information, such as images. The layman is typically at a first location, such as on a ship far from the shore, where it is impossible or too complicated to provide medical assistance, such as by flying in a doctor, by transporting the patient to shore, and so on. In addition means of communication are thereby inherently limited. It is therefore important that information of a patient, such as optical information on a condition of the patient, can be made available. Thereto the first mobile device comprises a first optical input, such as a camera. With the camera an image can be taken from a patient. The image can be send and thereby shared to the medical professional and displayed on a second mobile device, which second mobile device is comparable in characteristics and/or features with the first mobile device. Thereto both devices have implemented a two-directional transmitting system, wherein the transmitting system in use receives at least one layer of first optical input 31 from the first device relating to a physical reality from the first device and transmits the at least one layer of first optical input to the second mobile device and receives at least one layer of second optical input 32 relating to a physical reality from the second device from the second optical input and transmits the at least one layer of second optical input to the first mobile device. In addition thereto the first device in use displays second optical input of the second device superimposed over the first optical input, and wherein the second device in use displays first optical input of the first device subimposed over the second optical input, and wherein the displayed input on the first device is preferably equal or partly equal to the displayed input on the second device, that is the combined or merged inputs, either superimposed or subimposed, are equal to one and another. It is noted that the terms "superimposed" and "subimposed" are relative and in principle are considered interchangeable as long as the various layers of input are projected over one and another in a usable fashion. Therewith both devices are provided with at least one layer of augmented reality superimposed over an image representing reality at the first or second location, respectively. Therewith effectively the use of a first device and the user of the second device look at the same image, or at least part thereof; in other words the displayed images on the first and second devices respectively are the same, though the full display need not be used for displaying said images. The image may be displayed together with at least one further image, or not. The medical professional now can give input to the layman, such as directions, advice, can provide medical details, etc. which input can be directly seen by the layman. The present image may likewise relate to a continuous optical recording.

In principle more than one layer of optical and augmented reality can be provided to the first and/or second mobile device, such as 2-5 layers, such as 3-4 layers. A first layer may represent direct input, a second layer may represent input from a database, a third input may represent actions to be taken, a fourth input may represent graphical input, and so on.

The at least one layer of (first or second) optical input may be provided against a, for recording, neutral background, such as a blue background.

In addition to the above the use of the first or second device, respectively, can each independently switch layers of graphical input on or off, therewith increasing or reducing an amount of augmented reality. For instance a first use may look at the first reality and augmented reality layers 2 and 3 provided by the second user, whereas the second user looks at the first physical reality (being typically augmented reality layer 1 for the second device) and physical reality from the second device, and so on. Therewith the present system is very flexible and versatile.

In addition to the above the first and second user may each independently use further functionality of the mobile devices, such as audio, vibration, recording, measurement capabilities, etc.

Thereby the present invention provides a solution to one or more of the above mentioned problems.

Advantages of the present invention are detailed throughout the description.

DETAILED DESCRIPTION OF THE INVENTION

The present invention relates in a first aspect to a wireless communication system according to claim 1.

In an exemplary embodiment the present system may further comprise a tracking system for recording of instructions and actions performed.

In an exemplary embodiment of the present system the first optical input may be provided by a first camera, which may or may not use an additional optical system such as lenses.

In an exemplary embodiment of the present system the second optical input may be provided by a second camera that may or may not use an additional optical system such as lenses.

In an exemplary embodiment of the present system the first device and/or second device may display further optical input.

In an exemplary embodiment of the present system optical input may further be provided by a touch screen, a mouse pad, and graphics.

In an exemplary embodiment the present system may further comprise at least one further mobile device having a further optical input, and a (wireless) transceiver, and implemented thereon the two-directional transmitting system.

In an exemplary embodiment of the present system at least one location may be a remote location, such as remote from a shore, such as at least 200 km from a shore or remote from a medical professional, such as at least 200 km.

In an exemplary embodiment the present system may further comprise a digitally and/or physically accessible reference document or images, that may or may not be presented in an additional augmented reality layer, the reference document comprising in view of medical actions instructions for preparation thereof, instructions for triaging, instructions for diagnosing, instructions for performing measurements, instructions for carrying out, instructions for logging data, instructions for after care, a database, and an overview of contents, preferably organized in a layered manner. As such available, and typically regularly updated information, is directly available. In addition also artificial intelligence may be used to further support the layman.

In an exemplary embodiment the present system may further comprise a coordinator for establishing contact between the first mobile device and a second mobile device, wherein the coordinator selects the second device based on at least one of availability, distance, language capabilities of the owner, specific medical expertise of the owner, time zone, and stability of the transmitting system. As such the best available support can be delivered to a subject.

In an exemplary embodiment the present system may further comprise at least one of an identity checker, credentials checker, a unique session identifier, such as a calibration sticker. Therewith secured information can be transferred as well as information on the condition of the subject.

In an exemplary embodiment the present system may further comprise a data-logging system, and a sensor, such as a medical sensor, such as for ECG, blood pressure, for vital parameters, blood and urine analysis, and blood oxygen level. Therewith information on the treatment of a subject as well as details of the subject can be transmitted and stored.

In an exemplary embodiment the present system may further comprise a switch for activating or deactivating superimposed display on one or both devices. For some applications the superimposed display may interfere with a process of treating the subject and can better be switched off.

In an exemplary embodiment of the present system the second device may retrieve input from a database. Therewith the layman can be assisted directly by a computer or the like.

In a second aspect the present invention relates to a use of the present system for training and for providing real-time medical assistance.

The invention is further detailed by the accompanying figures and examples, which are exemplary and explanatory of nature and are not limiting the scope of the invention. To the person skilled in the art it may be clear that many variants, being obvious or not, may be conceivable falling within the scope of protection, defined by the present claims.

SUMMARY OF THE FIGURES

FIG. 1-3 show schematics of the present invention.

DETAILED DESCRIPTION OF THE FIGURES

Figure 1:
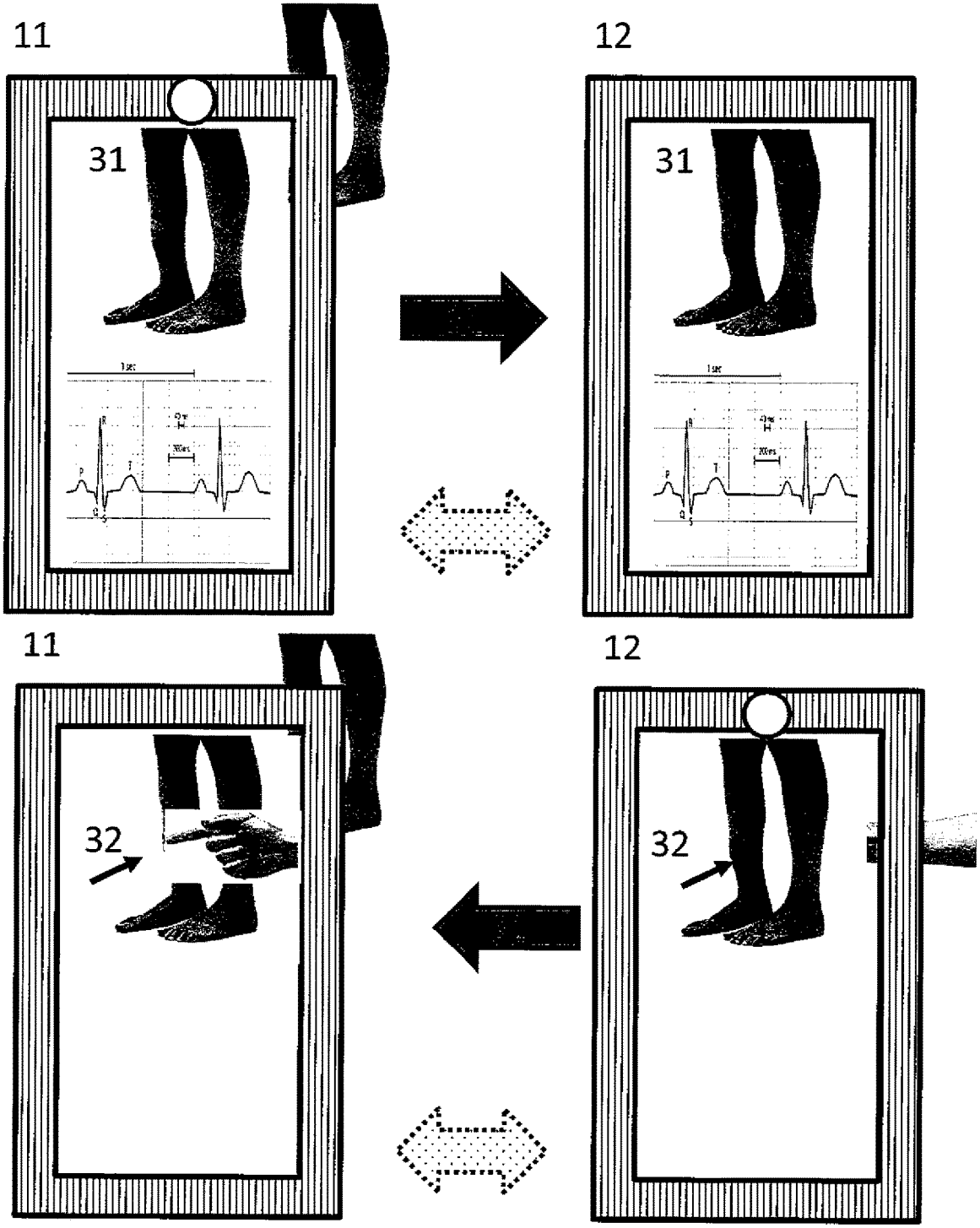

FIG. 1 shows schematics of the present invention. With respect to the first two schematics shown: Therein a person with a broken leg is shown representing a first reality. The present helper uses device 11 to take a picture 31. The picture, as well as an ECG, (representing augmented reality layer 1 of the second device) is transmitted to device 12 of the present professional, represented by the arrow directed to the right. Note that device 12 at this point has no (or a blank) image. Devices 11 and 12 are in contact with one and another (represented by the double headed arrow), typically real time contact (only involving a transmitting delay, if any). With respect to the third and fourth schematics shown: The professional looks at the image and ads input 32 to the picture 31 on his device 12 and points towards the fraction using his hand, representing a second reality. The input 32 is transmitted to device 11 (represented by the arrow directed to the right) and superimposed over the picture 31 on device 11. Likewise a superimposed image of input 32 (representing augmented reality layer 1 of the first device) and picture 31 is formed on device 12. Therewith a virtual reality is created in which the helper and professional look at the same image.

FIG. 2 shows a first and second location where mobile devices 11 and 12 are used to capture images of reality 31 and reality 32. On the top row each device, her mobile phone, captures an image. The system now combines images 31 and 32 (second row) into one overlaid image, which may be regarded as merged and presenting augmented reality. Both realities are augmented and super- or sub-imposed. Augmentation of reality 31 and 32 creates a third reality 33. The augmented reality, now represented as image 33, is made in the fourth row. In the fifth row each of the two devise is present with reality 33. Both users now can see the same augmented reality.

Figure 3:
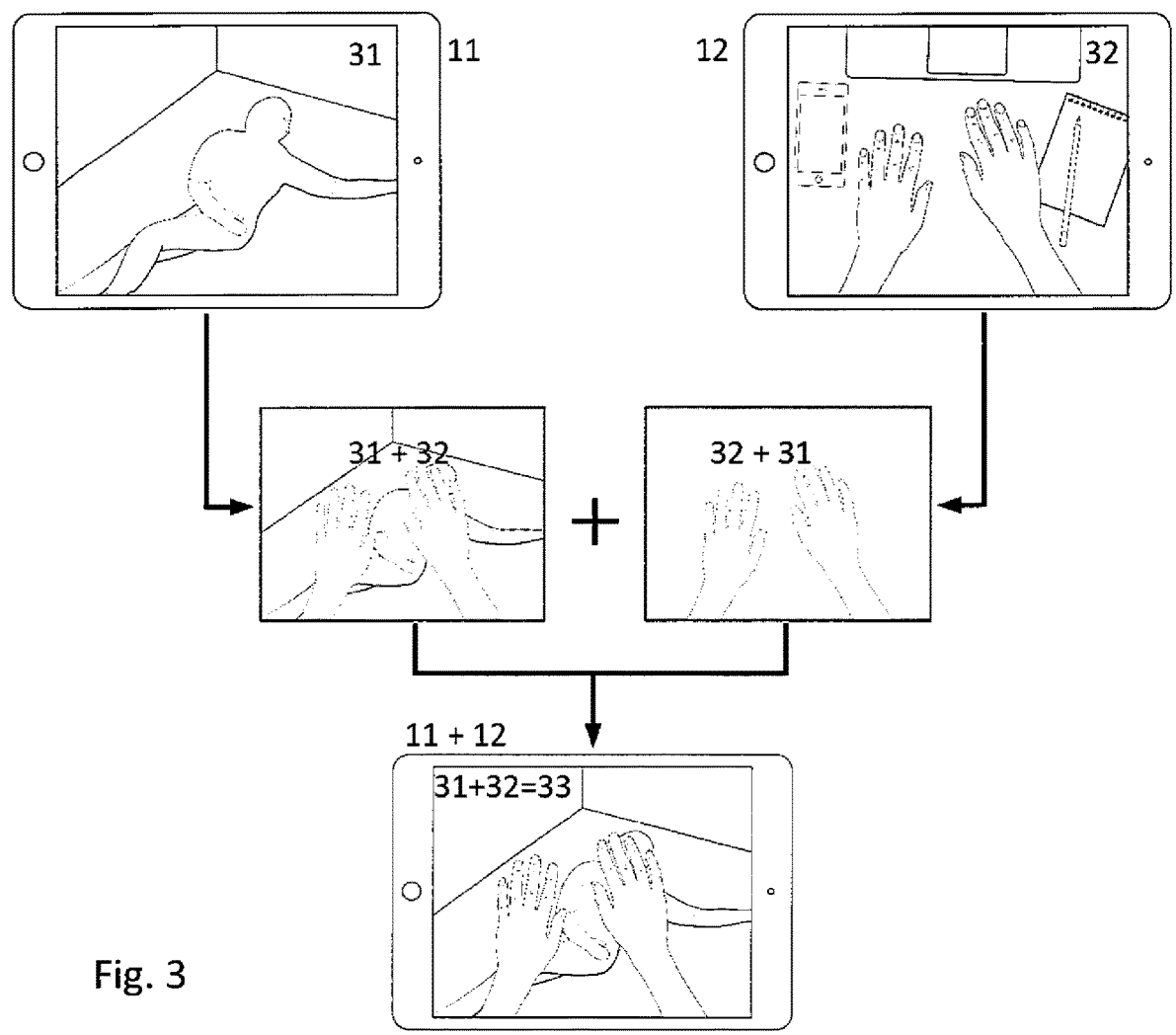

FIG. 3 represents an example of FIG. 2. On a first location, e.g. on a ship, a person is in need of medical care as observed by e.g. the ship's captain using a first device 11 taking an image 31 of a first reality. Contact is established with a user of mobile device 12, typically a doctor. She makes an image 32 of her hands representing a second reality 32. Both realities are augmented and super- or sub-imposed (middle frames). The image of the hands is superimposed or subimposed, respectively, such that e.g. a virtual treatment of the person in need is made visible; an augmented reality, now represented as image 33, is made in the third row, and the two devise are provided with this (same) reality 33. Both users now can see the same augmented reality. The captain now can follow the virtual reality closely in real life and treat the person in need accordingly.

EXAMPLES/EXPERIMENTS

The invention although described in detailed explanatory context may be best understood in conjunction with the accompanying examples.

Practical Example

Step by Step Instructions on Using AR System for Remote Medical Support

The example relates to a situation wherein Device 1 is on a remote location and Device 2 is a device on medical support location (doctor's device). Additional devices may be present, in so far as required and feasible and it may relate to any additional unit. It is the combination of devices (minimum two: device 1 and 2) that may be regarded as the present basic system.

In order to start the (both) devices should be powered up, meet minimum technical specifications, use a compatible software platform (Android/iOS/Windows/Linux etc.), have additional drivers and software installed for two-directional transmitting, be connected to the internet and/or have an IP address. When using the present AR-application/platform the two devices should connect, identify and use a secure connection.

The following steps are typically performed.
1) The person(s) using device 1 (hereafter: helper, typically a layman) and the person(s) using device 2 (hereafter: the medical professional, typically a doctor) and the patient or object (hereafter: the subject) can be positively identified by voice, vision, available ID or any other legal or required means.
2) If possible they agree to: their role and accept terms and conditions of use by 1) signing in with known and verified credentials of by 2) direct input (typing, touching, clicking) or clearly stating verbally and the patient/object responsible for accepting and consenting to the help offered.
3) Device 1 may be positioned either:
   static, using a fixing device that will hold device 1 in place,
   or dynamic, by being attached to the helper in their line of sight, using goggles or any other means to comfortably attach the device,
   or is positioned in such a way relative to subject, that the helper can work, manipulate and use instruments/tools on the subject, while keeping the subject in view/on screen of the device.
4) Device 2 may be positioned either:
   static, using a fixing device that will hold device 2 in place,
   or dynamic, by being attached to professional in their line of sight, using goggles or any other means to comfortably attach the device,
   or is positioned in such a way, that the professional can work, manipulate and use instruments/tools in front device while keeping the subject on screen of the device.
5) A calibration sticker can (but does not need to) be used: it has a unique session number, a colour calibration print and a fixed size for reference and will be placed close or next to the subject within the vision frame of device 1 (camera) and device 2 can calibrate after detection of the sticker.
6) By using device 2 the professional can in so far as required:
   make drawings, display pictures, project video(s) using device 2 as input device, by touching the screen, or using any input device (mouse, stylus, touchpad, controller, etc.) or retrieving pictures, images and video material from a database or any other source
   manipulate his hands, arms and any other part of his body, such as to indicate to the helper to perform certain actions, manipulate instruments of tools in such manner that the camera of device 2 captures these movements, pictures or projections, such as to provide a visual example.

7) These inputs created by the professional using device 2 can be projected on device 1 (and likewise device 2) onto an overlaying visual layer that results in a projection of the reality (the actual view of the subject, relating to a physical reality) with the visual (AR) layer (relating to at least one of a further physical reality, images, graphics, pictures, etc.) superimposed on the screen of device 1. The helper will see both the subject as well as the (superimposed) input made by professional on device 2.

8) By using device 1, the helper can see the subject (in reality and on screen), see directly what professional shows, explains, and/or instructs him to do (in AR overlay), see pictures, images, supporting information from database or any other source (in AR overlay), see video's on how to carry out certain skills and techniques (in AR overlay), can switch the AR layer on- and off on device 1, can see and train and prepare for copying and re-doing the manipulations and instructions shown by professional, and can execute or perform the manipulations, instructions or skills shown in the AR layer in reality on the subject.

9) The professional can see the subject, see the AR overlay as visible on device 1, including any visual input used, see any actions by helper, give directions and instructions to the helper, using voice, text, video and/or AR overlay, and can switch the AR layer on and off on device 1 and 2.

10) All actions on device 1 and 2 are logged and saved in a database.

In view of operation additional functionality may be added. For instance device 1 can have sensors attached, that will help to monitor the condition of subject. In case of a patient ECG, heartrate, blood pressure and other vital parameters can be monitored and made visible on device 1 and 2. The helper can use device 1 without a professional (no device 2) and using images, video's, explanations on skills and techniques retrieved from a database or any other source, that can be superimposed (via AR layer) on the subject. Using artificial intelligence and machine learning, the collected input from the database can be used to recognize, diagnose certain conditions and predict any required actions to be taken by helper.

The invention claimed is:

1. A symmetrical wireless communication system for medical assistance to a patient comprising:
    a first mobile device at a first location of a person in charge of providing medical care, the first mobile device comprising a first optical input for obtaining real-time optical input comprising first images from a first physical reality comprising the patient, a first display, and a first transceiver;
    a second mobile device at a second location of a medical professional, the second mobile device comprising a second optical input for obtaining real-time optical input comprising second images from a second physical reality of the medical professional, a second display, and a second transceiver;
    a two-directional transmitting system implemented on both the first and second mobile devices, wherein the two-directional transmitting system is configured to receive at least one layer of first optical input comprising the first images relating to the first physical reality comprising the patient from the first mobile device and is configured to transmit the at least one layer of first optical input to the second mobile device and is configured to receive at least one layer of second optical input comprising the second images relating to the second physical reality of the medical professional from the second mobile device and is configured to transmit the at least one layer of second optical input to the first mobile device;
    wherein the first mobile device is configured to display the at least one layer of second optical input of the second mobile device superimposed over the first optical input for forming an augmented first reality comprising the second images superimposed over the first images,
    wherein the second mobile device is configured to display the at least one layer of first optical input of the first mobile device subimposed under the second optical input for forming an augmented second reality comprising the first images subimposed under the second images,
    wherein the superimposed displayed inputs of the augmented first reality on the first mobile device is equal and symmetrical to the subimposed displayed inputs of the augmented second reality on the second mobile device, and
    wherein the second images from the second physical reality of the medical professional comprise medical input from the medical professional for the person in charge of providing medical care to the patient.

2. The wireless communication system according to claim 1, further comprising a tracking system for recording of instructions and actions performed.

3. The wireless communication system according to claim 1, wherein the first optical input is provided by a first camera.

4. The wireless communication system according to claim 1, wherein the second optical input is provided by at least one of a second camera, a graphical input, a video input, a touch screen, a mouse, a touch pad, a stylus, a controller, or a database.

5. The wireless communication system according to claim 1, wherein the first mobile device and second mobile device are configured to display further optical input.

6. The wireless communication system according to claim 1, wherein optical input is further provided by a touch screen, a mouse pad, and graphics.

7. The wireless communication system according to claim 1, comprising at least a third mobile device comprising an optical input and a wireless third transceiver, wherein the two-directional transmitting system is implemented on the third mobile device.

8. The wireless communication system according to claim 1, wherein at least one location is a remote location.

9. The wireless communication system according to claim 1, further comprising a digitally or physically accessible reference document, the reference document comprising in view of medical actions instructions for preparation thereof, instructions for triaging, instructions for diagnosing, instructions for performing measurements, instructions for carrying out, instructions for logging data, instructions for after care, a database, and an overview of contents.

10. The wireless communication system according to claim 1, further comprising a coordinator configured to establish contact between the first mobile device and the second mobile device, wherein the coordinator is configured to select the second mobile device based on at least one of availability, distance, language capabilities of an owner of the first mobile device, language capabilities of an owner of the second mobile device, specific medical expertise of the owner of the first mobile device, specific medical expertise of the owner of the second mobile device, time zone, and stability of the transmitting system.

11. The wireless communication system according to claim 1, further comprising at least one of an identity checker, credentials checker, a unique session identifier, a data-logging system, and a sensor, selected from a medical sensor for ECG, blood pressure, for vital parameters, blood and urine analysis, and blood oxygen level.

12. The wireless communication system according to claim 1, further comprising a switch for activating or deactivating superimposed display on one or both of the first and second mobile devices.

13. The wireless communication system according to claim 1, wherein the second mobile device is configured to retrieve input from a database.

14. A method of using a symmetrical wireless communication system comprising training and providing real-time medical assistance to a patient with a wireless communication system of claim 1, the method comprising:

providing the first mobile device at the first location of the person in charge of providing medical care, the first mobile device comprising the first optical input for obtaining optical input comprising first images from the first physical reality comprising the patient, the first display, and the first transceiver;

providing the second mobile device at the second location of the medical professional, the second mobile device comprising the second optical input for obtaining optical input comprising second images from the second physical reality of the medical professional, the second display, and the second transceiver;

providing a two-directional transmitting system implemented on both the first and second mobile devices, wherein the two-directional transmitting system is configured to receive at least one layer of first optical input comprising the first images relating to the first physical reality comprising the patient from the first mobile device and is configured to transmit the at least one layer of first optical input to the second mobile device and is configured to receive at least one layer of second optical input comprising the second images relating to the second physical reality of the medical professional from the second mobile device and is configured to transmit the at least one layer of second optical input to the first mobile device;

wherein the first mobile device is configured to display the at least one layer of second optical input of the second mobile device superimposed over the first optical input for forming an augmented first reality comprising the second images superimposed over the first images, and wherein the second mobile device is configured to display the at least one layer of first optical input of the first mobile device sub imposed under the second optical input for forming an augmented second reality comprising the first images sub imposed under the second images, wherein the superimposed displayed inputs of the augmented first reality on the first mobile device is equal and symmetrical to the sub imposed displayed inputs of the augmented second reality on the second mobile device, and providing the second images from the second physical reality of the medical professional comprising medical input from the medical professional for the person in charge of providing medical care to the patient.

* * * * *